United States Patent [19]

Kuntz

[11] Patent Number: 4,790,809
[45] Date of Patent: Dec. 13, 1988

[54] URETERAL STENT

[75] Inventor: David H. Kuntz, Los Angeles, Calif.

[73] Assignee: Medical Engineering Corporation, Racine, Wis.

[21] Appl. No.: 50,509

[22] Filed: May 14, 1987

Related U.S. Application Data

[63] Continuation-in-part of Ser. No. 770,689, Aug. 29, 1985, abandoned.

[51] Int. Cl.$^4$ ............................................. A61M 25/00
[52] U.S. Cl. ........................................ 604/8; 604/280; 604/281; 128/657
[58] Field of Search ....................... 604/43, 8, 55, 264, 604/280, 281; 128/1.3, 656, 657

[56] References Cited

U.S. PATENT DOCUMENTS

| 243,396 | 6/1881 | Pfarre. | |
|---|---|---|---|
| 3,042,030 | 7/1962 | Read | 128/127 |
| 3,043,309 | 7/1962 | McCarthy | 128/348 |
| 3,631,848 | 1/1972 | Muller | 128/2.05 R |
| 3,674,014 | 7/1972 | Tillander | 128/2.05 R |
| 3,831,585 | 8/1974 | Brondy et al. | 128/2 B |
| 3,961,632 | 6/1976 | Moossun | 128/347 |
| 3,986,493 | 10/1976 | Hendren, III | 128/1.3 |
| 4,063,561 | 12/1977 | McKenna | 128/351 |
| 4,212,304 | 7/1980 | Finney | 128/349 R |
| 4,244,362 | 1/1981 | Anderson | 128/200.26 |
| 4,270,542 | 6/1981 | Plumley | 128/350 R |
| 4,307,723 | 12/1981 | Finney | 128/349 R |
| 4,315,509 | 2/1982 | Smit | 128/303 R |
| 4,531,933 | 7/1985 | Norton et al. | 604/8 |

OTHER PUBLICATIONS

Poulton et al., "Seizure Associated with Induction of Anesthesia with Isoflurane" 1984 Anesthesiology 61:471-476.
Cooper, "Anesthesia Can be Safer" Jun. 1985, Medical Instrumentation, vol. 19: No. 3, 105-108.
Kimbrough et al., "Cardiac Rhythm in Men During Cystoscopy" 1975 Journal of Urology, vol. 113: 846-849.
Marier et al., "Gram-Negative Endocarditis Following Cystoscopy" 1978 The Journal of Urology, vol. 119: 134-137.
Rajendran et al., "Peripelvic Extravasation and Formation of Perinephric Urinoma after Cystoscopy" 1980 Urology, vol. XVI, No. 2: 199-201.
Walther et al., "Cytoscopy in Children" 1979 The Journal of Urology, vol. 122: 717-720.
"Perioperative Deaths" The Lancet, Nov. 9, 1985, p. 1049.
Forand et al., "Cardiac Arrest and Anaphylaxis with Anesthetic Agents" 1985 JAMA, vol. 254, No. 19, pp. 2741-2742.
Hezmall et al., "Controlled Endoscopic Retrieval of Ectopic Ureteral Catheters Using Fluoroscopic Guidance," Endourology, Urology, vol. XXV, No. 6, Jun. 1985, pp. 613-615.
IEEE Transaction on Magnetics, vol. MAG-6, No. 2 (Jun. 1970) Tillander, 128/657, pp. 355-358.

Primary Examiner—Stephen C. Pellegrino
Attorney, Agent, or Firm—Quarles & Brady

[57] ABSTRACT

An ureteral stent comprises an elongated, flexible tubular member which has one end with a magnetically attractable tip. Both ends of the stent are preferably both set in the form of hooks. A method of removing the stent from the bladder of a patient comprises introducing a retrieving catheter with a magnet at its proximal tip into the urethra, advancing the proximal tip of the catheter into the bladder which is signalled by urine flowing into the catheter, catching the magnetically attractable tip of the stent with the magnet and removing the stent by withdrawing the catheter with the magnetically attractable tip of the stent held by the magnet of the catheter.

4 Claims, 1 Drawing Sheet

U.S. Patent  Dec. 13, 1988  4,790,809
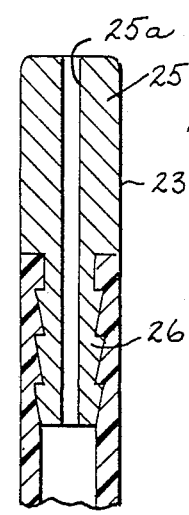
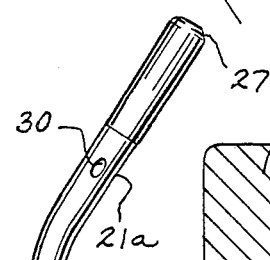
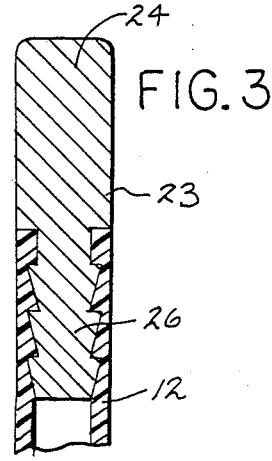
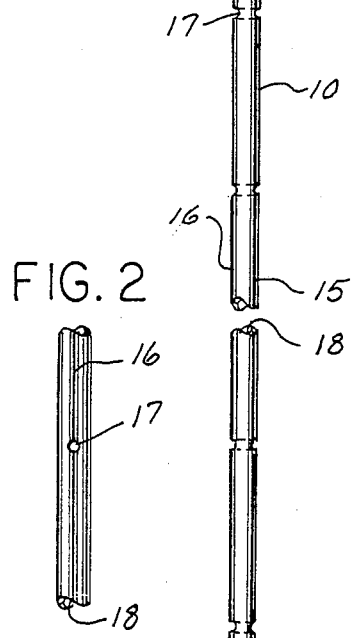
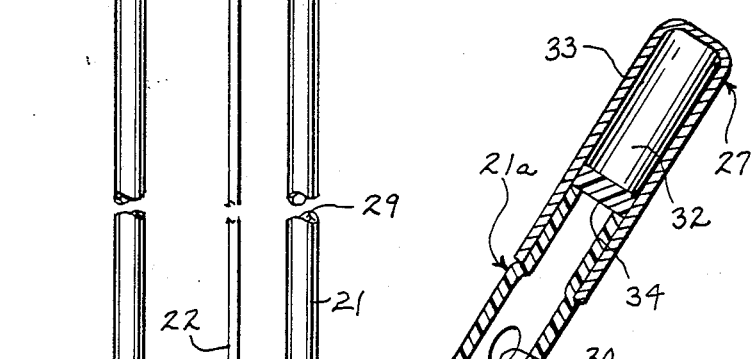
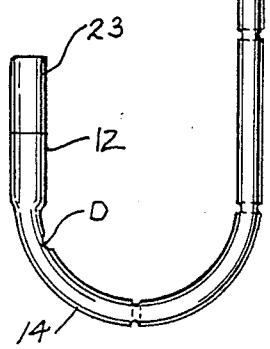

URETERAL STENT

RELATED CASE

This application is a continuation-in-part of my copending application Ser. No. 770,689 filed Aug. 29, 1985 now abandoned.

FIELD OF THE INVENTION

The present invention relates to ureteral stents. More particularly, it relates to a novel stent which can be more easily removed than existing stents.

BACKGROUND OF THE INVENTION

In dwelling ureteral catheter stents or drainage tubes have been used to bypass ureteral obstructions or ureterovaginal fistulas and maintain urinary drainage. In the past, stents made of straight lengths of open end tubing have been used for this purpose and have provided good drainage for sustained periods of time. However, the use of such open end tubing has not been completely satisfactory. For example, in some instances, the tubing has migrated and in others it has been expelled.

Various attempts have been made to produce stents which do not have the problems which accompany the use of such tubing. For example, stents have been designed which are closed at one end to facilitate passage into a body passage and which have at the other end a flange to make upward migration of the stent less likely. Another approach has been to provide the body of the stent with sharply pointed barbs which are designed to prevent downward migration and expulsion. However, such barbs increase the diameter of the stent making it more difficult to insert and in some instances can cause the stent to migrate outside the bladder.

In U.S. Pat. No. 4,212,304 issued July 15, 1979 and U.S. Pat. No. 4,307,723 issued Dec. 29, 1981, ureteral stents are disclosed which have hooks at each end which are urprisingly effective in preventing migration and expulsion. The patented stents are widely accepted because they can be easily introduced both endoscopically and during open surgery.

All the commercially available stents have one disadvantage in common; they are difficult to remove, especially from male patients. The usual method for removal of an indwelling stent from the ureter of a male is a complex and painful procedure which can require a general anesthetic.

SUMMARY OF THE INVENTION

It is an object of the present invention to disclose a novel ureteral stent which can be readily removed from the ureter of male or female patients.

It is another object to disclose a unique method of removing the novel stent from the ureter and a kit for practicing the method.

The ureteral catheter stent of the present invention can take many forms but preferably it comprises an elongated, flexible tubular member of substantially uniform outside surface throughout its length having proximal and distal ends which are set in the form of hooks and a distal end which is, at least in part, of a magnetically attractable material.

The main body of the stent is preferably made of a soft, flexible, radiopaque material and may be provided with indicating means which can be seen through a cystoscope and which will show the direction the proximal hook will extend when the stent is in place. In the preferred embodiment, the terminal portion of the distal end is closed by a tip of magnetic material. The tip is permanently affixed to the main body of the stent and may be covered with an outer layer of biocompatible material, if desired.

The stent is generally put in place by inserting a guide wire through the most distal opening and into the lumen. The guide wire is relatively stiff so that both of the hooks are straightened in the process. A stent pusher can be threaded over the free end of the guide wire behind the stent to aid the passage of the stent through a cystoscope. If an obstruction is encountered the ureteral stent employed has an open proximal end and the guide wire used has a yielding leading end which is smaller than the proximal end opening so that the guide wire can be maneuvered past the obstruction and the ureteral stent advanced over the guide wire and past the obstruction.

When for some reason it is desired to remove the indwelling stent, a retrieving catheter with a magnet is inserted through the urethra into the bladder and into proximity with the magnetically attractable tip at the proximal end of the stent. The catheter is maneuvered until the magnet catches the magnetically attractable tip at the distal end of the stent. The catheter with the stent attached is then completely removed from the patient. Alternatively, the catheter and stent combination can be withdrawn to a position at which the distal end of the stent can be caught with a retraction device, such as a forceps, and removed.

The method of removing an indwelling ureteral stent of the present invention can be done without surgical intervention or general anesthetic. Furthermore, it can be usually accomplished without even visualizing the stent.

The above stated and other objects and advantages of the invention will be apparent from the description which follows:

DESCRIPTION OF THE DRAWINGS

FIG. 1 is an elevational view of the preferred embodiment of the stent, the stent pusher, the retrieving catheter and the guide wire of the present invention;

FIG. 2 is an enlarged, partial side view of the stent of FIG. 1;

FIG. 3 is an enlarged view partly in section of the distal end of the stent of FIG. 1;

FIG. 4 is a view similar to FIG. 3 of the distal end of another embodiment of the stent of the invention;

FIG. 5 is an enlarged sectional view of the proximal end of the retrieving catheter; and FIG. 6 is an enlarged view showing the proximal end of the retrieving catheter magnetically attached to the distal end of the stent of FIG. 1.

DESCRIPTION OF THE PREFERRED EMBODIMENT

In the preferred embodiment shown in FIGS. 1 and 2, the stent 10 is seen to be an elongated tubular member having a proximal end 11 and a distal end 12. Portions adjacent each of the ends 11 and 12 are formed and set in the shape of gently curved hooks 13 and 14 which extend in opposite directions.

The two gently formed opposed hooks 13, 14 of the stent prevent it from migrating either upwardly or downwardly once it is in place. A suitable material may be incorporated into the hooks 13 and 14 to make them less flexible and therefore make the stent more resistant to migration. The hooks 13 and 14 extend in opposite directions so that when the stent 10 is used as an indwelling ureteral stent the proximal end 11 can hook into the lower calix or renal pelvis while the distal end 12 curves out into the bladder. This design also prevents the tip of the distal end of the stent from impinging directly into the bladder mucosa thereby decreasing discomfort and inflammation.

The stent 10 includes a relatively straight intermediate section 15 which extends between the proximal hook 13 and the distal hook 14. As seen best in FIG. 2, a guideline 16 is affixed to the side of the stent opposite the proximal hook 13. The guideline 16 helps the surgeon to determine cystoscopically or during open surgery the direction the proximal hook 13 will form when the guide wire is removed.

The main body of the stent 10 is made of a suitable flexible material such as nylon which is soft and stiff enough for the intended purpose and which preferably contains a radiopaque material. The stent may be supplied in 7 French and 8.5 French sizes in 16, 24, 26, 28 and 30 cm lengths. The listed length of the stent 10 is the length of the section 15 and does not include the hooked ends 13 and 14. Measurement points (not shown) may be affixed along the guideline 16 every 5 cms or so to assist the surgeon in estimating the ureteral length and selecting the proper stent for passage.

Still referring to FIG. 1, it can be seen that the stent 10 has radial drainage passages 17 which connect the lumen 18 of the stent 10 to the outside and permit inside/outside drainage. The drainage passages 17 are located about 2 centimeters apart on both sides of the straight section 15. The passages 17 of both sides are preferably aligned. There are similar but larger openings 19 in the inside wall of proximal hook 13 and an opening D adjacent the tip of the distal end 12.

In FIG. 1, there also can be seen a stent pusher 20, a retrieving catheter 21 and a guide wire 22 which is used to position the stent 10 in a body passage such as a ureter.

The stent 10 is normally supplied with the proximal end 11 closed; however, if desired it may be open. When normal endoscopic insertion is employed, the guide wire 22 is introduced into the lumen 18 of the stent 10 to straighten both hooks 13 and 14. When the proximal end 11 is open the guide wire can have a yielding leading tip (not shown) which can be passed through the proximal opening of the stent when an obstruction is encountered and used to maneuver the stent past the obstruction.

As seen in FIGS. 3 and 4, the distal end 12 of the stent 10 includes a tip 23 which is magnetically attractable. The tip 23 may be a rod 24 as seen in FIG. 3 or a cylinder 25 as seen in FIG. 4. The tip 23 is preferably of carbon steel which has a high iron content and good magnetic properties. To prevent corrosion when in contact with urine the entire tip is underplated with electroless nickel and gold plated. The tip 23 is provided with barbs 26 and force fit and/or glued to the main body of the stent. Other methods of attachment also may be used.

In use the guide wire 22 is threaded through either the opening D (seen in FIG. 1) when the tip 23 is the rod 24 or the lumen 25a of the cylinder 25 (seen in FIG. 4) to straighten the hooks 13 and 14. To assist in properly positioning the stent 10 in a ureter using a cystoscope, the stent pusher 20 is threaded over the free end of the guide wire 22. The stent pusher 20 is then used to advance the stent 10 into position. Once the stent 10 is properly positioned, the guide wire 22 and the stent pusher 20 are removed by withdrawing the guide wire 22 while holding the stent pusher 20 thus causing the stent 10 and stent pusher 20 to separate after which the guide wire 22 and then the stent pusher 20 are withdrawn.

As seen in FIG. 5, the proximal end 21a of the retrieving catheter 21 is formed in a coude bend. When it is desired to remove the preferred stent of the present invention, the retrieving catheter 21 with a magnet 27 at its proximal end 21a is introduced into the urethra with indicating means 28 facing the side of the body opposite the side where the stent is located. This insures the correct orientation of the magnet 27 towards the distal end 12 of the stent upon entry into the bladder. The user knows when the coude bend portion of the catheter 21 has entered the bladder because urine will then flow into the catheter lumen 29 via the drainage holes 30 and out the other end 31 of the catheter. The end 21a may be rotated in an arc until the magnet 27 catches the magnetically attractable tip 23 of the stent (as seen in FIG. 6).

The indicating means 28 on the catheter may be a stripe as seen in FIG. 1 or a spot or dimple which indicates the direction of the coude bend. The coude bend in addition to helping locate the distal end 12 of the stent also allows for easier passage of the catheter past the prostate and retrieval of the stent. The catheter 21 and stent 10 combination may then be completely withdrawn by withdrawing the catheter 21. Alternatively, the catheter 21 and stent combination may be withdrawn just enough for the distal end 12 of the stent 10 to be reached with a forceps or other grasping device. The described method of removing an indwelling stent is surprisingly successful even though it is accomplished without any visualization of the stent.

The ureteral stent 10 of the present invention is preferably made of silicone rubber. If a stiffer stent is preferred it may be made of a polymer which has a durometer between about 70 Shore 'A' and about 55 Shore 'D' to which 10% barium sulfate has been added as the radiopaque agent. Stents made of the latter material have been found to be soft enough not to cause undue discomfort to the patient and stiff enough to bypass obstructions in the ureter. Other plastic materials such as polyurethane which possess the desired properties and resist encrustation with urine salts can also be used.

The stent 10 is preferably formed by extruding a length of tubing of the desired size and durometer. The proximal end 11 of the tubing is then placed in a mold to close the lumen. The length of tubing is then placed in a form to shape the hooks 13 and 14. The drainage openings may be formed at any step of the process by piercing the wall of the tubing with a flattened, sharpened hole cutter of the desired size or by use of a laser or any other conventional means. The magnetically attractable tip is then force fit and/or glued or otherwise permanently attached to the remainder of the stent 10.

The ureteral stent 10 of the present invention may be supplied as a separate item or as a component of a kit. A kit might contain a stent 10 of the desired size, a stent pusher 20, a suitable guide wire 22 and a retrieving catheter 21 as seen in FIG. 1.

The stent pusher 20 may be supplied as a ready made component of the kit or a satisfactory stent pusher may be made from a half length of a relatively stiff standard ureteral catheter, preferably 5 French.

The retrieving catheter 21 which is approximately 16 Fr. or 0.215" in diameter is preferably of a relatively stiffer material then the stent 10 and it has a proximal end 21a with a coude bend (i.e. an angle of about 150°). The coude bend is about 1" long and there are fluid drainage passages 29 in the coude bend so that fluid can drain out through the catheter 21. The other end 30 of the catheter can be provided with an adapter (not shown) so that fluid can be injected into the bladder via the catheter to aid stent removal.

As seen best in FIGS. 5 and 6, the magnet 27 comprises a cylindrical core 32, preferably of neodymium-iron-boron material, within a protective stainless steel cap 33. The magnet 27 is secured to the end of the coude bend by crimping the steel cap 33 onto the catheter. The cap 33 serves to both attach the magnet 27 to the catheter 21 and to protect the core 32 from the destructive effects of urine in the bladder. The core 32 is protected from urine in the catheter lumen 29 by the seal 34 which can be formed of a silicone adhesive that also helps secure the magnet 27 in place.

In the preferred embodiment described and shown in the drawing, the proximal and distal ends of the catheter stent are both in the form of gently curved hooks. However, it is to be understood that the term "hook" is intended to include other functionally equivalent shapes which prevent migration and do not increase the effective outer diameter of the stent, or complicate its method of introduction.

It will be readily apparent to those skilled in the art that a number of modifications and changes can be made without departing from the spirit of the invention. For example, although in the preferred embodiment the magnetically attractable tip 23 and the magnet 27 are both of metal, one or both could be of magnetic ceramic, if desired. In addition, if a stronger magnet is desired, a small electromagnet could be used.

It also should be understood that it is within the scope of the invention to have the magnet on the distal end of the stent and the magnetically attractable material at the proximal end of the retrieving catheter; however, such an arrangement may not be as desirable. Finally, it is to be understood that in some instances it may be desirable to have a stent with a magnetically attractable proximal end so that it can be removed through a nephrostomy tract with a retrieving catheter. Therefore, it is to be understood that the scope of the invention is not to be limited by the foregoing description, but only by the claims.

I claim:

1. In a ureteral stent comprising an elongated, flexible, tubular member of substantially uniform outside diameter throughout its length and having at one end a hook for placement in the kidney and at the other end a hook for placement in the bladder, the improvement which comprises having a magnetically attractable tip at the other end of the stent, said tip being a cylinder of magnetically attractable material having a lumen through which a guidewire can be introduced into the tubular member.

2. A retrieving catheter for removing a ureteral stent with a magnetically attractable tip, said catheter being a tubular member having a lumen and one end which is of a size which can be introduced into the urethra of a patient, said catheter having a portion including said one end which is bent at an obtuse angle to the rest of the catheter, said bent portion including an opening through which urine can flow and means for magnetically attracting the magnetically attractable tip of a stent.

3. A retrieving catheter of claim 2 in which the means for attracting the tip of the stent includes a magnet which is protected from urine by a fluid tight seal that is between the magnet and the lumen of the catheter.

4. A method of retrieving from the urinary tract of a patient a ureteral stent which includes a magnetically attractable end and which is in the patient's bladder, said method comprising introducing into the urethra of the patient a retrieving catheter having means at its leading end for magnetically attracting the magnetically attractable end of the stent, advancing said catheter until is reaches the bladder of the patient, bringing said means into contact with the magnetically attractable end of the stent and then withdrawing the catheter with the stent attracted thereto through the urethra and out of the patient.

* * * * *